United States Patent [19]

Kinouchi

[11] Patent Number: 5,441,644
[45] Date of Patent: Aug. 15, 1995

[54] METHOD OF ISOLATION AND PURIFICATION OF TREHALOSE

[75] Inventor: Naoyuki Kinouchi, Kawasaki, Japan

[73] Assignee: Ajinomoto Co., Inc., Tokyo, Japan

[21] Appl. No.: 190,449

[22] Filed: Feb. 2, 1994

[30] Foreign Application Priority Data

Feb. 2, 1993 [JP] Japan ................................. 5-015614
Feb. 2, 1993 [JP] Japan ................................. 5-015616

[51] Int. Cl.$^6$ ............................................ B01D 61/00
[52] U.S. Cl. .................................... 210/651; 210/650;
210/660; 210/714; 210/638; 127/34; 127/46.2;
127/55; 127/58; 435/274; 435/276
[58] Field of Search ............... 210/638, 650, 651, 660,
210/714; 127/34, 46.2, 55, 58; 435/274, 276

[56] References Cited

U.S. PATENT DOCUMENTS 4,247,340  1/1981  Cartier .................................. 127/55
5,008,189  4/1991  Oroskar et al. ...................... 210/651

FOREIGN PATENT DOCUMENTS 0556838  8/1993  European Pat. Off. .
2671099  7/1992  France .
52285    5/1975  Japan .................................. 435/275

OTHER PUBLICATIONS

Patent Abstracts of Japan, vol. 17, No. 225 (C-1055)[5854], May 10, 1993, JP-A-4-360692, Dec. 14, 1992.

Primary Examiner—Robert A. Dawson
Assistant Examiner—Ana M. Fortuna
Attorney, Agent, or Firm—Oblon, Spivak, McClelland, Maier, & Neustadt

[57] ABSTRACT

A method for isolating and purifying trehalose from trehalose-containing solutions is described. Using ultrafiltration and selective concentration, highly pure crystals of trehalose dihydrate are obtained from aqueous solution.

9 Claims, 1 Drawing Sheet

METHOD OF ISOLATION AND PURIFICATION OF TREHALOSE

BACKGROUND OF THE INVENTION

1. Field of the Invention

The present invention relates to a method of isolating and purifying trehalose. Trehalose and its various hydrates are well known as cell activity-retaining agents, cold-resisting agents, an anti-freezing agents, etc. in the fields of medicine, biochemistry and food science.

2. Description of the Prior Art

Trehalose has been isolated by extraction from dry yeast or the like; by enzymatic production and isolation, and by the culturing of microorganisms. Regarding the extraction of trehalose from dry yeast, methods have been reported wherein trehalose is extracted with ether or alcohol followed by the repeated crystallization of the extracted trehalose with alcohol and acetone (Science, 61 (1587), 570, 1925); wherein trehalose is extracted from yeast by treatment with $NH_2SO_4$ and heavy metals ($HgSO_4+Fe_2(SO_4)_3$) and a large amount of 95% alcohol is added to the extract to crystallize trehalose (Science, 82 (2131), 422, 1935); wherein trehalose is extracted from yeasts with alcohol, ionic substances are removed with ion-exchange resins (Amberlite IR-100, IR-4B), and a large amount of 95% alcohol is added to the extract to crystallize trehalose (J. Am. Chem. Soc., 72, 2059, 1950), etc. However, as these methods require a plurality of complicated steps for purification, they are not suitable for mass-production or for producing large amounts of trehalose. In addition, the purity of the trehalose obtained by the above-described methods is low, as is their yield.

The enzymatic production of trehalose has been described wherein maltose is treated with a maltose phosphorylase and a trehalose phosphorylase to produce trehalose, precipitates are removed from the enzymatically treated liquid, and the product is purified by treatment with an anion-exchange resin (Japanese Patent Application Laid-Open No. 58-216695). The trehalose-containing liquid purified by treatment with an anion-exchange resin is then applied to a borate-type anion-exchange resin so that the trehalose is adsorbed thereto, and the adsorbed trehalose is eluted and fractionated with a potassium borate solution. The obtained trehalose fraction is treated with a cation-exchange resin and concentrated, the concentrated liquid is distilled after adding a lower alcohol thereto so as to remove boric acid therefrom, and thereafter this concentrate is repeatedly crystallized with alcohol to obtain crystals of trehalose dihydrate.

Alternatively, sucrose is treated with an immobilized glycosyl transferase to produce paratinose, which is crystallized and separated, and the mother liquid containing by-product trehalose is treated with an anion-exchange resin of a mixed sulfite/bisulfite type and treated with a cation-exchange resin of the Ca-type to purify and isolate trehalose (Japanese Patent Application Laid-Open No. 4-131090). However, since these methods require purification or treatment with ion-exchange resins, they are not suitable for mass-production or for producing a large amount of trehalose. In addition, the purity of the trehalose as produced by such methods is low.

The production of trehalose by culturing microorganisms has been described where trehalose-producing bacteria of the genus Nocardia were cultured, the cells were removed from the culture liquid, the culture liquid was treated with methanol, insoluble substances were removed by filtration, and trehalose was isolated from the filtrate (Japanese Patent Laid-Open Application No. 50-154485). In the disclosed method, the filtrate is treated twice each with an anion-exchange resin and a cation-exchange resin and then subjected to gel filtration followed by adsorption to and elution from active charcoal, and the resulting elutate is crystallized from ethanol repeatedly to obtain crystals of trehalose.

Also known is a method of culturing fungi of the genus Rhizoctonia, Sklerotium or the like, followed by separating the cells from the culture liquid, triturating the cells, extracting them with an aqueous trichloroacetic acid solution, and isolating trehalose from the resulting extract (Japanese Patent Application Laid-Open No. 3-130084). In the disclosed method, the extract is first treated with chloroform and ether to remove lipids and trichloroacetic acid, there it is treated with an ion-exchange resin and dried to solid by evaporation. The solid is dissolved in acetonitrile or the like, and the solution is subjected to silica gel chromatography to isolate trehalose. Alternatively, the cells are removed from the culture liquid, the resulting supernatant is concentrated and then subjected to chromatography (Bio-Gel P-2), the trehalose fraction thus obtained is treated with Dowex 50 and again subjected to chromatography (Bio-Gel P-2), and finally dried to solid by evaporation to obtain a dry product of trehalose (Agric. Biol. Chem. 52 (3), 867–868, 1988). However, since these methods require various chromatographic processes, they are not suitable for mass-production or for producing a large amount of trehalose. In addition, the purification methods require plural steps.

As mentioned above, known processes for isolating trehalose generally contain an alcoholic crystallization step. However, the crystals of trehalose dihydrate obtained by alcoholic crystallization are problematic in that they are fine and have a low purity.

OBJECTS OF THE INVENTION

One object of the present invention is to solve the above-mentioned problems found in the prior art and provide a method of easily isolating highly-pure crystals of trehalose dihydrate from a trehalose-containing solution, which method is suitable for both mass-production and for producing a large amount of trehalose dihydrate crystals. Other objects of the invention will become apparent in the course of the following detailed description.

DETAILED DESCRIPTION OF THE INVENTION

Figure 1:
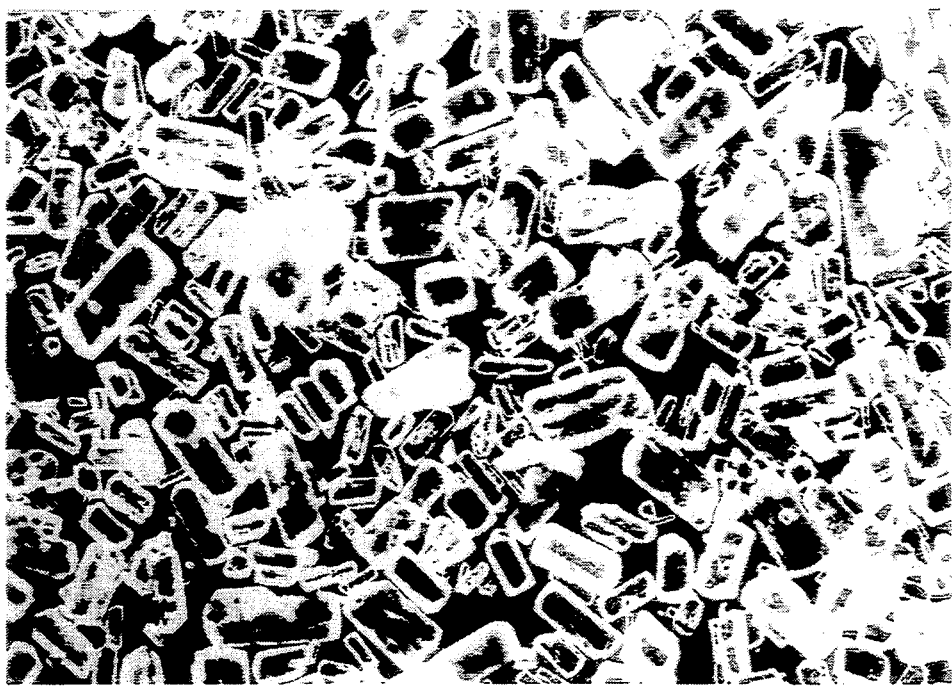
FIG. 1 is a photograph showing the crystal structure of the crystals of trehalose dihydrate obtained in Example 1 of the present invention.

The present invention relates to a method of isolating and purifying trehalose and all the hydrates thereof (including trehalose dihydrate) from a trehalose-containing solution which method is suitable for mass-production and for producing a large amount of pure trehalose. The invention method, which is industrially useful, inexpensive and efficient includes first subjecting a trehalose-containing solution to ultrafiltration preferably with an ultrafilter and then concentrating and preferably cooling the solution to crystallize trehalose dihydrate in and from the trehalose-containing solution so as to obtain highly-pure crystals of trehalose dihydrate in high yield.

The origin of the trehalose-containing solution to be processed by the present invention method is not limited. Preferably, it is an aqueous solution. For instance, useful in the present invention method are various trehalose solutions obtained as intermediates in various processes of producing, extracting, etc., trehalose from natural substances such as a dry yeast, a selaginella and the like; various aqueous trehalose solutions obtained as intermediates in various processes of obtaining trehalose by enzymatically converting maltose, sucrose or the like into trehalose; and various trehalose solutions obtained as intermediates in processes of obtaining trehalose by culturing microorganisms.

The processes of producing trehalose by culturing microorganisms may be any such known process like the one described above that utilizes known microorganisms of the genera Nocardia, Rhizoctonia and Sklerotium. In addition, various aqueous solutions derived from fermentation liquids obtained by culturing microorganisms belonging to the genus Brevibacterium, Corynebacterium, Microbacterium or Arthrobacter, which have heretofore been known as microorganisms that produce L-glutamic acid and other various amino acids in liquid media containing sucrose or maltose as the carbon source may be used. Any strain of these genera may be employed in the present invention, provided that they have an ability to produce trehalose. For instance, the following strains may be used:

*Brevibacterium lactofermentum* ATCC 13869
*Brevibacterium flavum* ATCC 14067
*Brevibacterium tibaricatum* ATCC 21642
*Corynebacterium glutamicum* ATCC 13032
*Corynebacterium acetoacidophylum* ATCC 13870
*Corynebacterium lylium* ATCC 15990
*Arthrobacter citreus* ATCC 11624
*Arthrobacter sulfureis* ATCC 15170
*Microbacterium ammoniaphylum* ATCC 15354

In addition, mutants derived from these strains and having elevated trehalose-producing ability can also be employed.

The cultivation of the microorganism is aerobic or anaerobic, preferably aerobic conditions. The temperature for the cultivation is suitably from 20° to 45° C. The pH of the culture liquid is preferably controlled from 5.0 to 10.0. For the pH adjustment, inorganic or organic acid or alkaline substances may be used as well as urea, calcium carbonate, ammonia gas, or the like. If desired, the cells may be separated from the fermentation liquid by conventional centrifugation or filtration before the liquid is processed by the present invention.

Where only the cells are desired to be substantially removed from the fermentation liquid, the liquid may be treated by ordinary centrifugation. Where high-molecular weight substances such as soluble proteins, etc. are desired to be removed along with the cells, the liquid may also be subjected to ultrafiltration with an ultrafilter. Where the fermentation liquid is treated by ordinary centrifugation, it may thereafter be desalted with an ion-exchange resin and then subjected to ultrafiltration with an ultrafilter or simply centrifuged and ultrafiltered.

Useful ultrafilters include ones that fractionate high-molecular weight substances having a molecular weight of about 1,000 daltons or more, typically 2,000, 3,000, 4,000 etc. daltons or more. Various known types of ultrafilters include those based on acetyl cellulose or similar cellulosic membranes, as well as polyamide, polysulfone, polyester, polyacrylonitrile, polyvinyl alcohol, polycarbonate, polyethylene, etc. membranes, and other various inorganic membranes. Any ultrafilter may be employed in the present invention, irrespective of the kind. Regarding the shape, any shape may be used. Preferred ultrafilters are of a flat membrane type or a module type. The latter module type is particularly preferred.

If the fermentation liquids or other trehalose-containing starting solutions contain substantial amounts of inorganic salts and/or other various ionic substances they are preferably removed prior to trehalose crystallization since such salts or ionic substances will precipitate during the crystallization. As the de-salting means, ion-exchange membranes and the like may be employed, but a simple method using a combination of a free-type cation-exchange resins and a free-type anion-exchange resin is preferred. The kinds of the cation-exchange resin and the anion-exchange resin to be used are not limited and any resin having a de-salting ability may be used irrespective of the kind. De-salting with ion-exchange resins may be conducted either before or after the ultrafiltration with an ultrafilter membrane. Prior to the crystallization of trehalose, it is preferred that the solution is decolored with an active charcoal or the like.

For crystallizing trehalose from an aqueous trehalose-containing solution, the solution is first concentrated to provide a dissolved trehalose concentration of approximately 50 to 100, preferably 60 to 80, more preferably 70 to 75 g/dl while the temperature of the solution is adjusted to about 20 to 100, preferably 40° to 80° C., and, optionally, fine powdery crystals of trehalose dihydrate are seeded to the concentrated solution to induce the generation or growth of new crystals. After the seeded or spontaneous generation and/or growth of new crystals, the slurry can be further concentrated to provide a total trehalose concentration of approximately from 75 to 100, preferably 85 to 93 g/dl total trehalose, and this further concentrated solution is gradually cooled to a temperature of from 5° to 20° C. to further grow the crystals. Then, the solution is allowed to stand for about 30 minutes to 2 hours to decrease or eliminate supersaturation, and it is then subjected to solid-liquid separation, and the crystals thus separated are washed with a small amount of water. In this way, highly-pure trehalose dihydrate crystals having a purity of 99% or more can be obtained. Trehalose itself may be produced by dehydrating the obtained trehalose dihydrate by any conventional method such as vacuum heating. Trehalose dihydrate crystals obtained by conventional crystallization from aqueous alcoholic solutions are small and fine (approximately 100 μm) and, when they are dissolved in water, the resulting aqueous solutions are not of high transparency. Trehalose dihydrate crystals obtained by the method of the present invention, however, have a high purity and, when they are dissolved in water, the resulting aqueous solutions are of high transparency.

Since trehalose has an extremely high solubility in water, a trehalose-containing solution could not previously be crystallized even after it had been concentrated. Even when concentrated by conventional methods, it becomes a caramel-like paste. In accordance with the method of the present invention, however, aqueous trehalose solutions are crystallized after having been previously filtered through an ultrafilter. Such solutions may then be crystallized to form trehalose dihydrate crystals therein. While not wishing to be held to a particular theory, it is believed that the reason the present method succeeds is because the substances which inhibit the crystallization of trehalose may be removed by the ultrafilter. Additionally, ionic substances and other impurities may be removed efficiently by the optional ion-exchange treatment with an ion-exchange resin, which may contribute to the problems of the prior art. In particular, when microorganisms which produce L-glutamic acid and other various amino acids are used for fermentation, large amounts of L-glutamic acid and other amino acids are produced in the fermentation liquid as by-products. By the method of the present invention, these amino acids may be removed by the ion-exchange treatment. Therefore, the present invention is free from the lowering of the purity of the product trehalose due to the amino acids.

Examples

Next, the present invention will be explained in more detail by means of the following examples. The purity of the product trehalose dihydrate was determined by high performance liquid chromatography (column: PA-03-S-5, manufactured by Yamamura Chemical Laboratories Co.).

Example 1

A liquid medium (pH 6.5) comprising 4% of glucose, 0.5% of urea, 0.1% of $KH_2PO_4$, 0.04% of $MgSO_4.7H_2O$, 300 μg/liter of thiamine hydrochloride, 300 μg/liter of biotin, 0.1% of concentrate liquid of soybean decomposate (as total nitrogen), 0.001% of $FeSO_4.7H_2O$ and 0.001% of $MnSO_4.4H_2O$ was prepared. The medium was placed in 500 ml-shaking flasks each in an amount of 20 ml/flask, and the flasks were sterilized at 110° C. for 10 minutes. One platinum loop of cells of Corynebacterium lylium ATCC 15990, which had been precultivated in a bouillon-agar slant medium for 48 hours at 31.5° C., were inoculated in the medium and were incubated at 31.5° C. for 24 hours by shaking culture using a reciprocating shaking incubator, to prepare a seed culture liquid.

A liquid medium that had been prepared by adding 2% of a 1/1 mixture of potassium chloride and ammonium chloride to a medium (pH 7.3) comprising 15% of sucrose, 0.1% of $KH_2PO_4$, 0.1% of $MgSO_4.7H_2O$, 300 μg/liter of thiamine hydrochloride, 300 μg/liter of biotin, 0.05% of concentrate liquid of soybean decomposate (as total nitrogen), 0.001% of $FeSO_4.7H_2O$ and 0.001% of $MnSO_4.4H_2O$ was put in one liter-jar fermenters and sterilized at 120 C. for 20 minutes. 15 ml of the seed culture liquid was inoculated to the media in the jar fermenters and incubated therein at 31.5° C. and at a stirring rate of 700 rpm under aeration of ½ vvm. During the culturing, the pH of the media was controlled at 7.3 by introducing ammonia gas thereinto. At the time when the turbidity of the 26-fold dilution of the culture liquid became 0.60 at 562 nm after the start of the culturing, 0.4 wt. % polyoxysorbitan monopalmitate was added to the medium and the culturing was continued further. Then, at the time when the sucrose in the culture liquid was completely consumed, culturing was terminated.

10 liters of the thus-obtained fermentation broth containing 400 g of trehalose (as trehalose dihydrate) and having a protein concentration of 2.0% were subjected to centrifugation to remove the cells therefrom (pH 7.8). Next, the cell-free broth was passed through a combination of a 10-liter H-type column of cation-exchange resin SK1B (manufactured by Mitsubishi Kasei Corp.) and a 20-liter OH-type column of anion-exchange resin WA30 (manufactured by Mitsubishi Kasei Corp.) connected in series, at a flow rate of 10 liter/hr, and 50 liters of a de-salted liquid were obtained. The de-salted liquid was filtered with an ultrafilter membrane SIP-0013 (fractionating molecular weight: 3000 daltons, manufactured by Asahi Chemical Co.) to obtain 60 liters of a permeate (having a protein concentration of 0.01%). Next, the permeate was pre-concentrated to have a trehalose concentration of about 35 g/dl, thus providing about 900 ml of a preconcentrate. 30 g of a powdery active charcoal was added to the preconcentrate and stirred for 2 hours at 60° C. whereby the preconcentrate was decolored. By filtration, the decolored filtrate was obtained. The decolored filtrate was further concentrated with a rotary evaporator under reduced pressure to provide a trehalose concentration of about 75 g/dl. About 2 g of fine crystals of trehalose dihydrate (size: 10~20 μm) were added thereto with stirring, and after about 30 minutes, this solution was cooled to 5° C. at a cooling rate of 5° C./hr. Crystals of trehalose dihydrate formed and they were separated by centrifugation and dried in a reduced-pressure drier at 40° C. for 15 hours. 178 g of crystals of trehalose dihydrate (pillar-like crystals having a purity of 99.5%) were obtained. 7 grams of the crystals were dissolved in one dl of water to form an aqueous solution of trehalose. The transmittance of the solution at a wavelength of 400 nm through a 10 mm-cell was 99.8%. As shown in FIG. 1 (×50), the grains of the crystals were large and uniform.

Example 2

5 kg of crude crystals (purity=90%) of trehalose dihydrate obtained by crystallization from an aqueous alcoholic solution were dissolved in water. The aqueous solution was filtered with an ultrafilter membrane (fractioning molecular weight: 3000 daltons) and the filtrate was concentrated to provide a trehalose concentration of 40 g/dl in the same manner as Example 1. 500 g of a powdery active charcoal were added thereto and stirred for 2 hours at 60° C. whereby the solution was decolored. By filtration, 15 liters of a decolored filtrate were obtained. The decolored filtrate was concentrated under reduced pressure to provide a trehalose concentration of about 75 g/dl. About 20 g of fine seed crystals of trehalose dihydrate (size=10~20 μm) were added thereto with stirring, and after about 30 minutes, this solution was cooled to 5° C. at a cooling rate of 5° C./hr. The thus-formed crystals were separated by centrifugation and dried in a reduced-pressure drier at 40° C. for 15 hours, and 2.7 kg of crystals of trehalose dihydrate (pillar-like crystals having a purity of 99.6.%) were obtained. These crystals were analyzed, and the data obtained are shown below.

TABLE 1

| Properties | Condition for Analysis | Analyzed Data |
|---|---|---|
| Loss on Drying | Drying under reduced pressure, 60° C., 2 hours | 9.2% |
| Residue on Ignition | | 0.02% |
| Specific Rotation | C = 7, water, $[\alpha]^D 20$ | 179.90° |
| State of Solution (transmittance) | C = 7, water, 400 nm, 10 mm cell | 99.9% |

As shown above, when 7 grams of the crystals were dissolved in 1 dl of water to form an aqueous solution the transmittance of the solution through a 10 mm-cell at a wavelength of 400 nm was measured and showed a transmittance of 99.9%. The grains of the crystals were uniform.

Comparative Example 1

110 ml of the fermentation broth containing 4.4 g of trehalose (measured as trehalose dihydrate) and having a protein concentration of 2.0% that had been obtained in Example 1 was subjected to centrifugation (for removing the cells) and then to ion-exchange treatment in the same manner as in Example 1. The cell-free broth was then concentrated and crystallized in the same manner as in Example 1, but the ultrafiltration step was omitted. Crystals of trehalose dihydrate were obtained. However, the crystals were obviously finer than those obtained in Example 1, and they were aggregated crystals. The purity of the crystals was 90%, and the yield thereof was 3.3 g. As compared with the trehalose dihydrate obtained in Examples 1 and 2, the purity and the yield were lower.

Comparative Example 2

2.2 liters of the fermentation broth containing 88 g of trehalose (as trehalose dihydrate) and having a protein concentration of 2.0% that had been obtained in Example 1, was subjected to centrifugation to remove the cells therefrom (pH 7.8).

Figure 2:
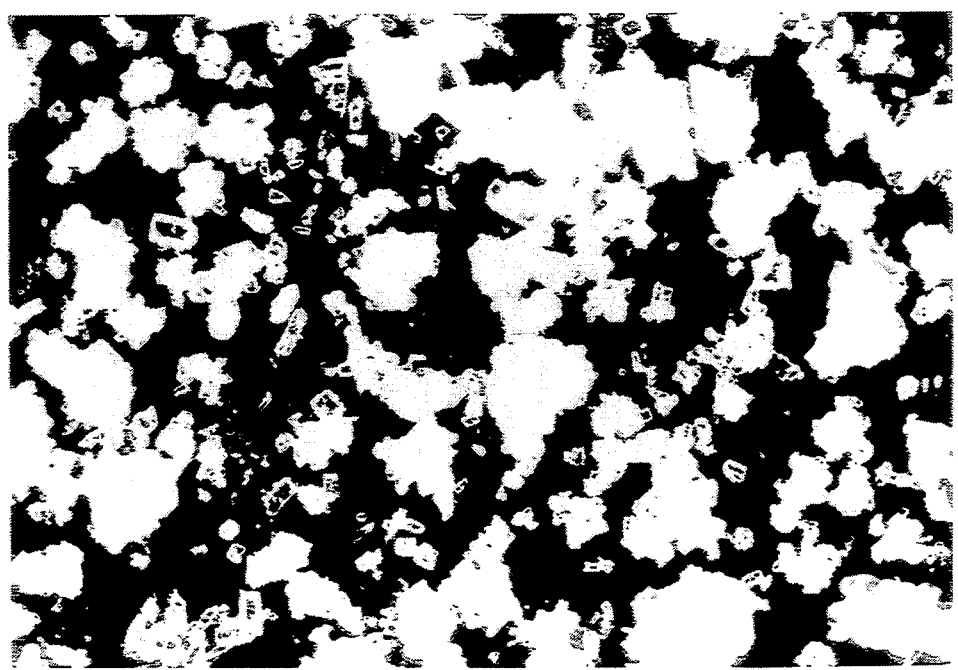
FIG. 2 is a photograph showing the crystal structure of the crystals of trehalose dihydrate obtained in Comparative Example 2.

The cell-free broth was passed through a combination of a 2-liter H-type column of cation-exchange resin SK1B (manufactured by Mitsubishi Kasei Corp.) and a 5-liter OH-type column of anion-exchange resin WA30 (manufactured by Mitsubishi Kasei Corp.) connected in series, at a flow rate of 2 liter/hr, and 5 liters of a de-salted liquid were obtained. The de-salted liquid was subjected to an ultrafiltration membrane SIP-0013 (fractionating molecular weight: 3000, manufactured by Asahi Chemical Co.) to obtain 10 liters of a filtrate (having a protein concentration of 0.01% or less). Next, the filtrate was concentrated to have a trehalose concentration of 35 g/dl. 900 ml of 100% ethyl alcohol was gradually added to the concentrated trehalose solution, with stirring. During the course of the addition of the alcohol, seed crystals of trehalose dihydrate were also added to the solution for crystallizing trehalose. This solution was cooled to 5° C. The crystals thus formed were separated by centrifugation and dried in a reduced-pressure drier at 40° C. for 15 hours, and 75 g of highly-pure trehalose dihydrate crystals (pillar-like crystals having a purity of 95% and a specific rotation $[\alpha]_{20}$ (NaD ray) of +178.9°) were obtained. The grains of the crystals were fine and not uniform, as shown in FIG. 2 (×50). These were inferior to the crystals obtained in Example 1.

By using the method of the present invention, a large amount of highly-pure crystals of trehalose dihydrate may be easily isolated and purified from a trehalose-containing solution, particularly from a trehalose containing fermentation liquid. The method of the present invention is suitable for mass-production and for producing large amounts of trehalose crystals.

What is claimed as new and desired to be secured by Letters Patent of the United States is:

1. A method of isolating and purifying trehalose dihydrate from a trehalose-containing solution, comprising the steps of subjecting the trehalose-containing solution to ultrafiltration obtain a permeate and concentrating the permeate to crystallize crystals of trehalose dihydrate therefrom.

2. The method of claim 1, wherein the permeate is concentrated to 50–100 g/dl of dissolved trehalose.

3. The method of claim 1, wherein ultrafiltration is accomplished with an ultrafilter membrane having a fractionating molecular weight of approximately 3000 daltons.

4. The method of claim 1, wherein the concentrated permeate is an aqueous solution that contains no water-miscible alcohols.

5. The method of claim 1, further comprising the step of adding crystals of trehalose dihydrate as seed crystals to the concentrated permeate.

6. The method of claim 1, further comprising the step of cooling the concentrated permeate.

7. The method of claim 1, further comprising the step of subjecting a trehalose-containing solution to an ion-exchange treatment prior to concentration.

8. The method of claim 7, wherein the ion-exchange treatment is prior to ultrafiltration.

9. The method of claim 7, wherein the ion-exchange treatment is after ultrafiltration.

* * * * *